US00PP17015P2

(12) United States Plant Patent
Ui et al.

(10) Patent No.: US PP17,015 P2
(45) Date of Patent: Aug. 22, 2006

(54) ***CALIBRACHOA* PLANT NAMED 'KAKEGAWA S79'**

(50) Latin Name: ***Calibrachoa* sp.**
Varietal Denomination: Kakegawa S79

(75) Inventors: Akinobu Ui, Iwata (JP); Toshimi Ohga, Kikugawa (JP)

(73) Assignee: Sakata Seed Corporation, Yokohama (JP)

( * ) Notice: Subject to any disclaimer, the term of this patent is extended or adjusted under 35 U.S.C. 154(b) by 143 days.

(21) Appl. No.: 11/052,158

(22) Filed: Feb. 7, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Jondle & Associates P.C.

(57) ABSTRACT

'Kakegawa S79' is a new *Calibrachoa* cultivar particularly distinguished by having yellow flowers with red veins and a semi-creeping growth habit.

1 Drawing Sheet

Figure 1:
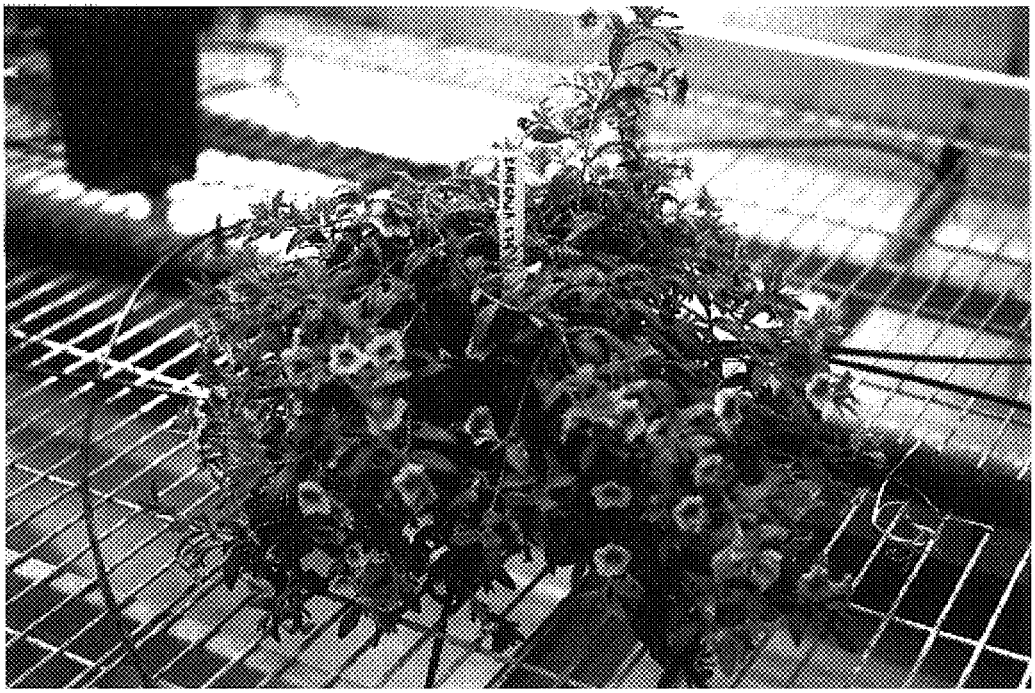

Genus and species: *Calibrachoa* sp.
Variety denomination: 'Kakegawa S79'.

BACKGROUND OF THE INVENTION

The present invention comprises a new and distinct cultivar of *Calibrachoa,* botanically known as *Calibrachoa* sp., and hereinafter referred to by the cultivar name 'Kakegawa S79'. It is characterized by having yellow flowers with red veins. The new cultivar originated from a hybridization made in Kakegawa, Japan in 2001. A proprietary *Calibrachoa* breeding line with apricot flowers and a semi-upright growth habit (female) was crossed with a proprietary *Calibrachoa* breeding line with red flowers and a semi-upright growth habit (male).

In August 2001, $F_1$ seed from the above hybridization was sown in the greenhouse. Three single-plant selections were made regardless of flower color and growth habit and intercrossed to produce $F_2$ seed. In February 2002, $F_2$ seed was sown and 100 total plants were evaluated. Four single-plant selections with bronze vein flower color and a semi-creeping growth habit were selected and vegetatively propagated. In the summer of 2002, these four selections were evaluated in a greenhouse and in an open field. One single plant was chosen based on trial results and asexually propagated through rooted plant cuttings in both Kakegawa, Japan and Salinas, Calif. 'Kakegawa S79' has been shown to reproduce true to type in successive generations of asexual propagation.

Description of the Genus *Calibrachoa* Llave & Lex

The genus *Petunia* was originally established in 1803 by A. L. Jussieu, who described both *P. parviflora* and *P. nyctaginiflora* as type species. Using a non-horticultural system that selected the first mentioned species as the type species (lectotype), N. L. Britton and H. A. Brown declared *P. parviflora* as the type species for *Petunia* in 1913.

During the 1980's and 1990, H. J. Wijsman published a series of articles regarding the ancestry of *P. hybrida,* the Garden *Petunia,* and the inter-relationship of several species classified as *Petunia.* These studies discovered that *P. hybrida* and its ancestral species, *P. nyctaginiflora* (=*P. axillaris*) and *P. violacea* (=*P. integrifolia*), possessed 14 pairs of chromosomes while several other species, including *P. parviflora,* possessed 18 pairs of chromosomes. Since *P. parviflora* was the lectotype species for the *Petunia* genus, Wijsman and J. H. de Jong proposed transferring the 14 chromosome species to the genus *Stimoryne.* Horticulturists opposed reclassifying the Garden *Petunia* and in 1986, Wijsman proposed the alternative of making *P. nyctaginiflora* the lectotype species for *Petunia* and transferring the 18 chromosome species to another genus. The I. N. G. Committee adopted this proposal. By 1990 Wijsman had transferred several species, including *P. parviflora* (=*C. parviflora*) to *Calibrachoa,* originally established by Llave and Lexarza in 1825. *Calibrachoa parviflora* (=*C. mexicana* Llave & Lexarza) is now the type species for the genus *Calibrachoa.*

Classification of the current *Petunia* and *Calibrachoa* species is still in progress. New species are also being identified. Consequently a proper description has not been written for the *Calibrachoa* genus. *Calibrachoa* can, however, be distinguished from *Petunia* based on the higher chromosome number, chromosome morphology, plant branching habit and type of flower bud aestivation. Whereas *Petunia* species bear a flower peduncle and one new stem from a node, *Calibrachoa* bear a flower peduncle and three stems. *Petunia* species have a cochlear corolla bud, and a single outermost petal covers the other four, radially folded and terminally contorted petals. *Calibrachoa* flower buds are flat with all five petals linearly folded and the two lower petals forming a cover around the three other petals and fused together.

DESCRIPTION OF PHOTOGRAPHS

This new *Calibrachoa* plant is illustrated by the accompanying photographs which show the plant's form, foliage and flowers. The colors shown are as true as can be reasonably obtained by conventional photographic procedures.

FIG. 1. shows overall plant habit.

Figure 2:
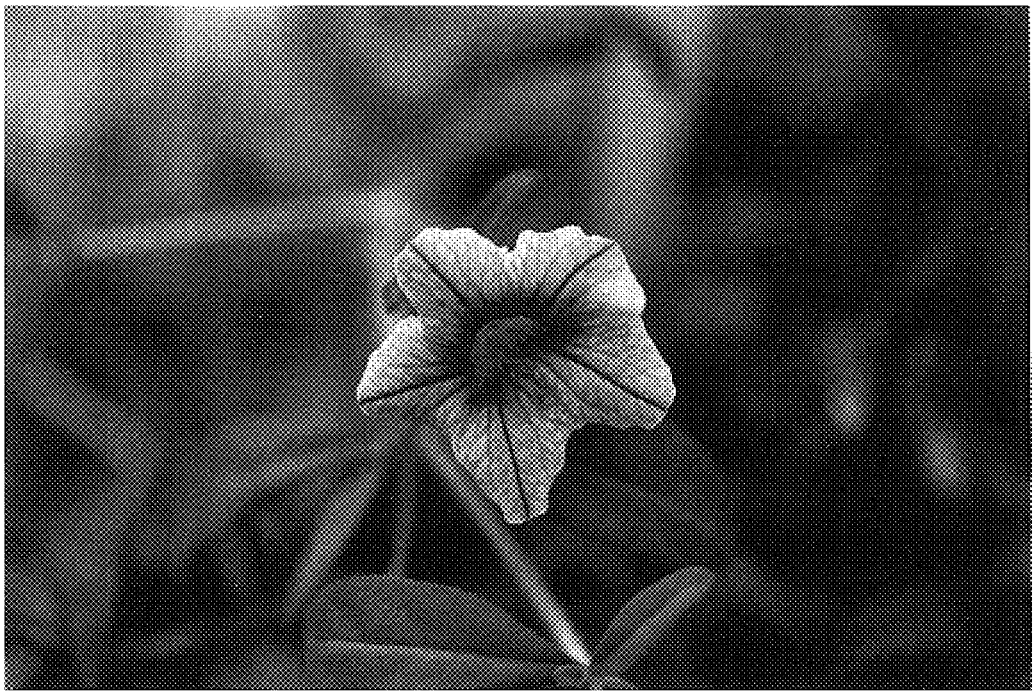

FIG. 2. shows the mature flower.

DESCRIPTION OF THE NEW CULTIVAR

The following detailed description sets forth the distinctive characteristics of 'Kakegawa S79'. The data which define these characteristics were collected from asexual reproductions carried out in Salinas, Calif. The detailed description was taken from plants grown under greenhouse conditions for approximately 4 months from transplanting of rooted cuttings. Color references are to The R.H.S. Colour Chart of The Royal Horticultural Society of London (R.H.S.), 4$^{th}$ Edition.

DETAILED BOTANICAL DESCRIPTION

Classification:
- *Family.*—Solanaceae.
- *Species.*—*Calibrachoa* sp. Cultivar 'Kakegawa S79'.
- *Common name.*—*Calibrachoa.*

Parentage:
- *Female.*—Unnamed and unknown proprietary *Calibrachoa* breeding line.
- *Male.*—Unnamed and unknown proprietary *Calibrachoa* breeding line.

Plant description:
- *Life cycle.*—Tender Perennial.
- *Form.*—Branching.
- *Habit.*—Semi-decumbent (mounding).
- *Height.*—20 cm as measured from soil level to top of plant.
- *Spread.*—55 cm.

Propagation:
- *Type cuttings.*—Vegetative cuttings.
- *Time to produce a rooted cutting.*—5–6 weeks.
- *Time to bloom from propagation.*—10 weeks after root development.

Environmental conditions for plant growth: The terminal 1.0–1.5 inches of actively growing stems were excised and the base of each cutting dipped for one to two seconds in a 1:9 solution of DIP 'N GROW root inducing solution immediately prior to placing the cutting into a cell tray. The cell tray contained a moistened peat moss-based growing medium. The cuttings were misted with water from overhead for 10 seconds every 30 minutes until sufficient roots were formed. Rooted cuttings were transplanted and grown individually in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow-release fertilizer containing 20% nitrogen, 10% phosphorous and 18% potassium. The typical average air temperature was 24° C.

Stems:
- *Stem color.*—RHS 143C (green).
- *Anthocyanin color.*—RHS 77A (purple).
- *Pubescence.*—Heavy.
- *Pubescence color.*—RHS 155A (white).
- *Stem description.*—Ancipital (round).
- *Stem diameter.*—0.4 cm.
- *Stem length.*—1.5–2.0 cm from soil line to first node.
- *Internode length.*—3.0–3.5 cm.

Leaves:
- *Leaf arrangement.*—Alternate.
- *Leaf shape.*—Elliptical.
- *Leaf apex.*—Mucronate.
- *Leaf base.*—Decurrent.
- *Leaf margin.*—Entire.
- *Leaf surface.*—Rough, dull.
- *Leaf surface pubescence.*—Slight.
- *Pubescence color.*—RHS 155A (white).
- *Venation.*—Pinnate.
- *Leaf length.*—3.5 cm.
- *Leaf width.*—1 cm.
- *Leaf color.*—Upper surface: RHS 137A (green). Lower surface: RHS 138B (green).
- *Petiole length.*—0.3 cm.
- *Petiole color.*—RHS 145A (yellow-green).

Inflorescence:
- *Flowering habit.*—Indeterminate.
- *Flower type.*—Solitary.
- *Flowering requirements.*—Will flower so long as day length is greater than 12 hours and temperature exceeds 13° C.
- *Duration of flowers.*—About 5 days.
- *Corolla shape.*—Flowers are funnel-shaped with five fused petals and five fissures dividing the petals.
- *Fragrance.*—Absent.

Flower buds:
- *Bud surface.*—Pubescent.
- *Bud length.*—1.8 cm.
- *Bud diameter.*—0.5 cm.
- *Bud shape.*—Ovate.
- *Bud color.*—RHS 160A (gray-yellow) with RHS 77C (purple) veins.
- *Peduncle length.*—3 cm.
- *Peduncle color.*—RHS 144A (yellow-green).

Flower description:
- *Flower depth.*—2.2–2.5 cm.
- *Flower tube length.*—1.2–1.6 cm.
- *Flower tube diameter.*—0.5 cm.
- *Flower diameter.*—3 cm.
- *Calyx.*—5 sepals, free.
- *Sepals.*—Shape: Lanceolate. Apex: Mucronate. Margin: Entire. Sepal color: Upper surface: RHS 136A (green) at tip fading to RHS 135C (green) at base. Lower surface: RHS 137B (green).
- *Petal shape.*—Spatulate.
- *Petal length.*—1 cm.
- *Petal width.*—1.5 cm.
- *Petal apex.*—Truncate.
- *Petal margin.*—Entire.
- *Petal texture.*—Glabrous.
- *Petal color.*—Lobe color: Upper surface: RHS 7C (yellow) with RHS 46A (red) midvein and RHS 34B (orange-red) veins. Lower surface: RHS 34A (red) fading to RHS 7C (yellow) with RHS 46A (red) veins. Corolla tube color: Inner: RHS 13A (yellow) with RHS 77A (purple) veins. Outer: RHS 160B (gray-yellow) with RHS 77A (purple) veins.

Reproductive organs:
- *Stamen number.*—5, free.
- *Stamen color.*—RHS 138A (green).
- *Pollen color.*—RHS 5A (yellow).
- *Ovary.*—Superior.
- *Pistil number.*—1 per inflorescence.
- *Pistil length.*—1.41 mm.
- *Stigma color.*—RHS 144A (yellow-green).
- *Style length.*—1.125 mm.
- *Style color.*—RHS 144A (yellow-green).

Disease and insect resistance: 'Kakegawa S79' has excellent resistance to rain, heat and drought, although it will not tolerate temperatures below 10° C. 'Kakegawa S79' is susceptible to *Botrytis,* powdery mildew, various stem and root rots, and certain viruses, such as Tobacco Mosaic Virus and *Impatiens* Necrotic Spotted Virus. 'Kakegawa S79' is also susceptible to aphids, leafminers, whiteflies and various *Lepidoptera.*

Comparison with Known Cultivars

*Calibrachoa* 'Kakegawa S79' is a distinct variety of *Calbrachoa* due to its yellow flowers with red veins. 'Kakegawa S79' is distinguished from known cultivars mainly by flower color as shown in Table 1 below.

TABLE 1

| Characteristic | 'Kakegawa S79' | '0B-10AA-1A' | '9B-8AA-1A' |
|---|---|---|---|
| Flower color | Yellow with red veins | Apricot | Red |

'Kakegawa S79' is most similar to the variety 'Kakegawa S52' (U.S. Plant Pat. No. 15,046); however, there are differences in flower petal color and corolla tube color as described in Table 2 below.

TABLE 2

| Characteristic | 'Kakegawa S79' | 'Kakegawa S52' |
|---|---|---|
| Petal color, upper surface | RHS 7C (yellow) with RHS 46A (red) midvein and RHS 34B (orange-red) veins | RHS 48C (red) with RHS 47A (red) mid-veins |
| Petal color, lower surface | RHS 34A (red) fading to RHS 7C (yellow) with RHS 46A (red) veins | RHS 50A (red) |
| Outer corolla tube color | RHS 160B (gray-yellow) with RHS 77A (purple) veins | RHS 6A (yellow) |

We claim:

1. A new and distinct cultivar of *Calibrachoa* plant as shown and described herein.

* * * * *